United States Patent [19]

Weisang et al.

[11] 4,152,246

[45] May 1, 1979

[54] CATALYZED PROCESSES FOR THE HYDROTREATMENT OF HYDROCARBONS

[75] Inventors: Joseph E. Weisang; Philippe Engelhard, both of Le Havre, France

[73] Assignee: Compagnie Francaise de Raffinage, France

[21] Appl. No.: 816,548

[22] Filed: Jul. 18, 1977

Related U.S. Application Data

[63] Continuation-in-part of Ser. No. 690,908, May 28, 1976, which is a continuation-in-part of Ser. No. 525,675, Nov. 20, 1974, Pat. No. 3,974,097.

[30] Foreign Application Priority Data

Nov. 23, 1973 [FR] France .............................. 73 41827
May 28, 1975 [FR] France .............................. 75 16703
Jul. 21, 1976 [FR] France .............................. 76 22233

[51] Int. Cl.$^2$ .......................... C10G 35/08; C07C 5/24
[52] U.S. Cl. .................................. 208/139; 585/419; 585/482
[58] Field of Search ................ 208/139; 260/673.5, 260/668 A

[56] References Cited

U.S. PATENT DOCUMENTS

| | | | |
|---|---|---|---|
| 3,806,446 | 4/1974 | Hayes | 252/441 |
| 3,928,177 | 12/1975 | Hayes | 208/139 |
| 4,026,959 | 5/1977 | Kemme et al. | 260/668 A |
| 4,048,099 | 9/1977 | Hayes | 208/139 |
| 4,062,903 | 12/1977 | Jacobson | 260/668 A |

*Primary Examiner*—C. Davis
*Attorney, Agent, or Firm*—Curtis, Morris & Safford

[57] ABSTRACT

The processes of the present invention employ catalysts in the hydrotreatment of hydrocarbons and comprise, on a refractory inorganic oxide support, the following metals:
  (a) from 0.02 to 2% of at least one platinum metal;
  (b) from 0.02 to 2% of at least one metal belonging to the group consisting of zirconium, titanium, and tungsten;
  (c) from 0.02 to 2% tin.

This catalyst is preferably halogenated, typically with chlorine, from 0.4 to 2%.

The preferred process according to this invention is the isomerization of a charge of alkylaromatic hydrocarbons, and particularly those having eight carbon atoms. The preferred isomerization catalyst is a platinum, tin and zirconium trimetallic catalyst halogenated with chlorine approximately from 1 to 2% based on the total catalyst weight.

The preferred isomerization process is practiced in at least two successive stages with the contacting of the catalyst taking place in at least one of said stages; and especially under the following conditions:
  (a) Pressure: Comprised between 3 and 40 bars.
  (b) Temperature: Comprised between 250° and 550° C.
  (c) Molar ratio of hydrogen to hydrocarbons: Comprised between 3 and 15.
  (d) Overall space velocity (v/v/h), measured in the liquid state: Comprised between 0.5 and 4, and preferably between 1 and 2.5.

Said catalysts are also useful for hydroreforming and aromatizing being surprisingly superior for all these types of reactions.

62 Claims, 4 Drawing Figures

FIG. 1

CATALYZED PROCESSES FOR THE HYDROTREATMENT OF HYDROCARBONS

This application is a continuation-in-part of parent application Ser. No. 690,908, filed May 28, 1976; which in turn is a continuation-in-part of grandparent application Ser. No. 525,675, filed Nov. 20, 1974, now issued as U.S. Pat. No. 3,974,097 on Aug. 10, 1976; which applications, including the corresponding French priority applications, are hereby fully incorporated by reference.

The present invention relates to catalysts intended for the hydrotreatment of hydrocarbons, and more particularly to petroleum cuts whose distillation range corresponds to that of gasolines and naphtha. It also concerns a process of preparing and using such catalysts.

The additional subject matter of the first CIP application, Ser. No. 690,908, relates to the hydrotreatment of hydrocarbon charges; and more particularly, the isomerization of alkylaromatic hydrocarbons.

The further subject matter of the present CIP application additionally teaches said isomerization being carried out in at least two stages.

The grandparent application (Ser. No. 525,675) discloses as follows.

By catalytic hydrotreatment processes are meant processes applied to hydrocarbon charges in the presence of hydrogen and which employ hydrogenation - dehydrogenation, isomerization, cyclization, dehydrocyclization and aromatization reactions. These reactions may exist simultaneously, as in the case of the hydroreforming of naphtha; however, depending on the nature of the charge, the reaction conditions, and the nature of the catalyst, one of these reactions may be preponderant, for instance the hydro-isomerization.

The great current development of processes for the catalytic hydrotreatment of hydrocarbons is known. It is due on the one hand to the necessity of the refineries to have a source of gasoline of very high octane number which is used either directly or, more generally, after mixing with a petroleum cut having a similar boiling range but of lower octane number, and on the other hand the necessity to have a source of aromatic hydrocarbons in petrochemical plants, since they are important raw materials of the petrochemical industry.

The metals of group VIII of the periodic table of elements, and particularly platinum, deposited on an acid or slightly acid refractory inorganic oxide, are extensively used as hydrotreatment catalysts.

It is known that in order to increase the octane number of the resultant efflux and the output of liquid, particularly the output of aromatic hydrocarbons without having to increase the platinum content substantially, one has been led to use bimetallic and trimetallic catalysts, among which, mention may be made by way of example, of:

(Pt - Sn), (Pt - Pb), (Pt - Ge), (Pt - Re), (Pt - Ir), (Pt - Au), (Pt - Cu), (Pt - Sn - Re), (Pt - SN - Ir), (Pt - Sn - Ge), (Pt - Pb - Re), (Pt - Ge - Re), (Pt - Re - Ir).

In addition of different metals makes it possible to obtain hydrotreatment catalysts which are of great interest.

The purpose of the present invention is therefore to obtain catalysts for the hydrotreatment of hydrocarbons which impart to the efflux a better octane numer and assure a higher yield of liquid than that obtained when using a catalyst which comprises only platinum or a platinum metal deposited on a refractory inorganic oxide.

In the present description, the expression "platinum metal" designates one of the following metals:
ruthenium
rhodium
palladium
osmium
iridium
platinum.

A preferred embodiment of the present invention is a catalyst comprising a support of a refractory inorganic oxide and admitting of a halogen element present in combined form, the said catalyst being characterized by the fact that it comprises the following metals in free or combined state:

a. 0.02 to 2% and preferably 0.10 to 0.70%, referred to the total weight of the catalyst, of at least one platinum metal;

b. 0.02 to 2% and preferably 0.02 to 0.60%, referred to the total weight of the catalyst, of at least one metal of the group consisting of tungsten, zirconium and titanium;

c. 0.02 to 2% and preferably 0.05 to 1.00%, referred to the total weight of the catalyst, of tin.

Said percentages being calculated with respect to the elemental form.

The invention concerns more particularly the catalysts defined above and in which:

d. the said support has a specific surface of more than 15 $m^2/g$ and a specific pore volume of more than 0.1 $cm^3/g$;

e. the halogen content is between 0.4 and 2%, and preferably 0.5 to 1.5%, referred to the total weight of the catalyst.

Another embodiment of the present invention is a process of preparing the hydrotreatment catalysts defined above, this process being of the type comprising at least one impregnation of the porous support with at least one solution containing at least one of the elements to be deposited, said process being characterized by the fact that at least one of the impregnation solutions contains either cations formed from the elements tungsten and/or titanium and/or zirconium or anions containing the elements tungsten and/or titanium and/or zirconium.

Another embodiment of the present invention relates to an improvement in the process of preparation described above, consisting of subjcting the catalysts, prior to use, to reduction and possibly presulfurization.

Finally a further embodiment of the invention concerns the application of the above-defined catalysts to the reforming of a charge of hydrocarbons.

The catalyst supports in accordance with the invention are the refractory substances customarily used for hydrotreatment catalysts. They have a sufficient specific surface and specific pore volume, the specific surface being preferably between 15 and 350 $m^2/g$ and the specific pore volume greater than 0.1 $cm^3/g$. These products should furthermore be of an acid or slightly acid character, such as alumina for instance. Alumino-silicates are also suitable.

The catalysts can be prepared by processes of impregnating the support with solutions containing the elements to be deposited. The applicants have found that it is advantageous to effect the depositing of the platinum last, after having effected the depositing of tungsten and/or of titanium and/or of zirconium; this first deposit being capable of being effected before, during, or after the deposit of tin.

The most advantageous catalysts are those whose contents of platinum metals, of metals of the group consisting of zirconium, tungsten and titanium, and of tin are between 0.02 and 2% and preferably 0.10 to 0.70%; 0.02 to 2% and preferably 0.02 to 0.60%; and 0.02 to 2% and preferably 0.05 to 1.00%; respectively.

The content of platinum metal is that customarily employed in multi-metallic catalysts for the hydrotreatment of hydrocarbons. In order to obtain satisfactory catalytic properties, the content of this type of metal is preferably greater than 0.10% but, for reasons of the cost of the catalyst, the said content is in general limited to 0.70%.

Likewise, the content of metal of the group consisting of zirconium, titanium and tungsten is between 0.02 and 2%. Below 0.02%, the improvement in the properties of the ordinary catalyst, comprising only one metal such as platinum deposited on a porous support, is not substantial, and it is not of interest either to exceed 2%. The applicants have furthermore observed that the most effective contents are those which are between 0.02 to 0.60%; since, above 0.60%, the increase in the cost of the catalyst is not compensated for by a sufficiently substantial improvement in the catalytic properties.

The same is also true of the tin. The content of this metal may vary between 0.02 and 2%; however, a content of 0.05 to 1% is advantageous, for the same reasons as those set forth above.

The halogen content of the catalyst is well-known in the art. It may vary between 0.4 and 2%, but the best results are obtained with halogen contents of 0.5 to 1.6%, chlorine being the preferred halogen; these quantities are calculated as if said halogen was in an elemental form; in fact it may be combined with the support and/or with the elements deposited on the support.

The acidity of the support may be modified, prior to the depositing of the elements or between the deposits when the latter are not simultaneous. The support on which the zirconium and/or the titanium and/or the tungsten and the tin have been deposited can be subjected in particular to a treatment with an acid, hydrochloric acid for instance, before depositing the platinum. This treatment will be described below in connection with the examples.

The applicants have observed that in the impregnation solution containing the elements titanium andor zirconium and/or tungsten and in the impregnation solution containing the tin, these elements may be in different states. Thus they may be in the state of cations having a stable degree of oxidation under the operating conditions and medium; for example, $W^{6+}$, $Ti^{4+}$, $Zr^{4+}$, $ZrO^{2+}$, $Sn^{4+}$. They may also be part of the constitution of anions, for example $WO_4^{2-}$, $TiO_4^{4-}$, $Zr_2O_7^{4-}$. The halogen present in the catalyst in accordance with the invention will generally be chlorine, in combined form; the combinations of the halogen may be with the support and/or with the elements deposited on the support.

Furthermore, the applicants have observed that a treatment of the catalyst prior to its use, said treatment consisting in effecting a reduction at about 500° C. — as in the case of most hydrocarbon hydrotreatment catalysts — and a presulfurizing of the catalyst, which presulfurizing may be effected at about 370° C. by hydrogen sulfide diluted in hydrogen, for instance; substantially improves the stability with time of the catalytic properties. This treatment, on an industrial plane, is of great interest since it has the effect of lengthening the period of use of the catalyst without having to regenerate it by the means known in the art.

The present invention is illustrated by the following examples, which are given solely by way of illustration. Example 1 concerns the hydroreforming of normal heptane. This particular charge does not constitute a limitation on the scope of use of the catalyst in accordance with the invention, but they can be used successfully for the hydroreforming of a charge of hydrocarbons whose boiling point is between 35 and 250° C. and whose sulfur content is less than 10 ppm and, if possible, 1 ppm. Example II concerns the aromatization of normal hexane. Like the normal heptane in the case of the hydroreforming, this particular charge is not limitative. As can be seen from Example III, the catalysts may be successfully used for te aromatizing of petroleum cuts comprising, primarily, molecules having six or seven carbon atoms in particular.

In all the examples, unless otherwise indicated, the compositions of the catalysts are expressed in % by weight of the catalyst.

EXAMPLE 1

An alumina is used in the form of extrudates, having the following characteristics:

| | |
|---|---|
| average diameter of the extrudates: | 1.5 mm |
| specific surface | 190 m²/g |
| pore volume | 0.51 cm³/g |
| average radius of the pores | 53 A° |
| chlorine content (measured by X fluorescence) | 0.5% by weight of the alumina |

This alumina is calcined for four hours at 600° C. It will constitute the support for the catalyst prepared and tested in the presented example. This example comprises the preparaton of a control catalyst TO and nine catalysts I to IX.

PREPARATION OF THE FIRST CONTROL CATALYST TO 100 g of the above alumina are immersed in 250 cc of an 0.1 N solution of hydrochloric acid. The alumina is then contacted with a circulating solution of hexachloroplatinic acid whose initial platinum content is such that the final catalyst contains 0.35% to 0.40% platinum.

After draining and then drying at 100° C., the solid is calcined at 530° C. in a muffle furnace. The catalyst thus contains 0.35% platinum and 1.37% chlorine.

PREPARATION OF THE CONTROL CATALYSTS T1, T2, T3, T4

100 g of the support alumina are immersed in 125 cc of solution containing 10 cc of hydrochloric acid RP. There are then added 125 cc if a second solution also containing 10 cc of hydrochloric acid RP and a given quantity of compound of the metal which it is desired to deposit, in such a manner as to obtain the desired contents in the final catalyst. The particles of alumina are drained, dried at about 100° C., and then calcined at 600° C. in a muffle furnace. The calcining temperature should be preferably above 500° C. The solid obtained is then treated with 250 cc of an 0.1 N hydrochloric acid solution and then contacted with a solution of hexachlorplatinic acid whose initial platinum concentration is such that the final catalyst still contains about 0.35% platinum. After draining and then drying at about 100°

C. the solid is calcined at 530° C. in a muffle furnace. The different compositions of the catalysts obtained are set forth in Table I.

PREPARATION OF CATALYSTS I, II, III

The catalyst I (Pt-Sn-Ti), II (Pt-Sn-W) and III (Pt-Sn-Zr) are prepared in a manner similar to catalysts T1, T2, T3. The only difference in the precedent manner of operation is that tin is also deposited on the support, and impregnation solution containing tin being mixed with the impregnation solution containing the titanium, the zirconium or the tungsten. The depositing takes place therefore simultaneously in this case. All the other operations are the same. The compositions of the catalysts prepared in this manner are given in Table I.

Catalytic tests described below are then carried out: 25 cc of catalyst are placed in a stainless steel reactor, a stream of pure dry hydrogen is passed over the catalyst for 2 hours, the temperature of the catalyst being maintained close to 500° C. and the pressure in the reactor being maintained at 7 bars. Thereupon, the temperature is brought to about 510° C. and the charge consisting of normal heptane is introduced with a liquid hourly space velocity of 2, and a ratio of the number of hydrogen moles introduced, to the number of normal heptane moles introduced, of 5.

Samples taken from the effluent of the reactor make it possible to determine, on the one hand, the liquid output by simple weighing and, on the other hand, the equivalent octane number of the liquid by application to the chromatographic analyses of the liquid of the ASTM mixture numbers appearing on normographs.

The tests are carried out with a fixed octane number, that is to say as soon as a decrease in the octane number is noted the temperature of the reactor is increased so as to obtain again the octane number originally selected. The variation of the temperature as a function of time is very substantially assimilatable to a straight line, the slope of which is measured, the smaller the slope of this line the better the catalyst, since it is then sufficient to modify the temperature only very slightly in the course of time in order to obtain the desired octane number. The limit temperature of use is therefore reached more slowly and the duration of the cycle of use is lengthened, which is an undeniable advantage at the industrial level.

In Table II the results of the tests thus carried out are indicated for three initially selected octane numbers for the catalysts included in Table I.

TABLE II

| Test Catalyst | Octane No. Selected | Initial Temp. (° C.) | Slope of the T = f (time) | Average Yield |
|---|---|---|---|---|
| T0 | 98 | 495 | 0.333 | 55.7 |
|  | 103 | 499 | 0.343 | 61.0 |
|  | 108 | 507 | 0.310 | 55.8 |
| T1 | 98 | 505 | 0.175 | 60.7 |
|  | 103 | 505 | 0.145 | 60.2 |
|  | 108 | 507 | 0.224 | 58.8 |
| I | 98 | 502 | 0.071 | 63.3 |
|  | 103 | 504 | 0.155 | 63.15 |
|  | 108 | 514 | 0.133 | 62.0 |
| T2 | 98 | 507 | 0.125 | 57.8 |
|  | 103 | 506 | 0.083 | 58.1 |
|  | 108 | 507 | 0.252 | 56.7 |
| II | 98 | 504 | 0.075 | 59.2 |
|  | 103 | 509 | 0.116 | 63.0 |
|  | 108 | 520 | 0.150 | 59.0 |
| T3 | 98 | 504 | 0.087 | 61.3 |
|  | 103 | 506 | 0.138 | 61.3 |
|  | 108 | 512 | 0.264 | 53.4 |
| III | 98 | 500 | 0.055 | 62.0 |
|  | 103 | 507 | 0.058 | 59.9 |
|  | 108 | 510 | 0.127 | 58.5 |
| T4 | 98 | 503 | 0.134 | 61.35 |
|  | 103 | 513 | 0.164 | 61.0 |
|  | 108 | 515 | 0.205 | 60.05 |

TABLE I

| Catalyst | Metal compound used in the first impregnation solution | % Pt | % Cl | % Sn | % Ti | %W | % Zr |
|---|---|---|---|---|---|---|---|
| T0 |  | 0.35 | 1.37 |  |  |  |  |
| T1 | Ti oxalate | 0.35 | 1.39 |  | 0.09 |  |  |
| I | Ti onalate + stannous chloride | 0.38 | 1.29 | 0.20 | 0.13 |  |  |
| T2 | Ammonium paratungstate | 0.35 | 1.05 |  |  | 0.28 |  |
| II | Ammonium paratungstate and stannous chloride | 0.38 | 1.29 | 0.20 |  | 0.27 |  |
| T3 | Zirconyl nitrate | 0.35 | 0.98 |  |  |  | 0.15 |
| III | Zirconyl nitrate + stannous chloride | 0.36 | 1.28 | 0.20 |  |  | 0.18 |
| T4 | Stannous chloride | 0.37 | 0.86 | 0.21 |  |  |  |

From this table it is seen that the trimetallic catalysts I, II and III are as a whole better than the bimetallic catalysts T1, T2, T3 or T4 and the monometallic catalyst T0. In particular, it is noted that they are more stable for average yields obtained, which are at least equivalent in most of the cases.

EXAMPLE II

This example illustrates the use of the catalysts in accordance with the invention for a specific chemical reaction occurring already in reforming, as mentioned in the specification, namely aromatization.

For this purpose 3 catalysts of the type of the invention were prepared. Three formulas are involved here, comprising platinum, tin, and zirconium or tungsten or titanium deposited on an alumina identical to the support of Example I by a method of impregnation similar to that described in the preceding example.

The catalysts thus prepared contain:
catalyst IV: 0.35% Pt; 0.20T Sn; 0.20T Zr; 1.13% Cl.
catalyst V: 0.37% Pt; 0.20% Sn; 0.13% Ti; 1.19% Cl.
catalyst VI: 0.36% Pt; 0.19% Sn; 0.23% W; 1.26% Cl.

With these three catalysts tests are carried out under atmospheric pressure at 520° C. with normal hexane (which is transformed into benzene by aromatization) and hydrogen, the latter being introduced with the normal hexane in the ratio:
hydrogen/normal hexane = 15.9

It is found that with the above three catalysts the conversion is practically complete, the benzene selectivity being 60.8 for catalyst IV, 68.4 for catalyst V, 64.6 for catalyst VI.

This shows that the catalysts of the invention are good aromatization catalysts.

EXAMPLE III

This example illustrates the use of a catalyst in accordance with the invention in an aromatization process carried out under pressure.

The catalyst employed contains:

0.35% by weight platinum (deposited by a solution of hexachloroplatinic acid)

0.21% by weight tin (deposited by a solution of stannous chloride)

0.16% by weight zirconium (deposited by a solution of zirconyl nitrate)

0.84% by weight chlorine.

In order to test the catalysts prepared in this manner for the aromatization reaction, there are employed two charges: the analysis of which is given in Table III.

TABLE III

| Components | Charge A (% by weight) | Charge B (% by weight) |
|---|---|---|
| iso-hexanes | 22.0 | 19.85 |
| normal-hexane | 27.8 | 25.0 |
| iso-heptanes | — | — |
| normal-heptane | — | — |
| methyl-cyclopentane | 23.8 | 28.3 |
| cyclohexane | 16.1 | 16.65 |
| benzene | 10.3 | 10.8 |
| paraffins (P) | 49.8 | 44.85 |
| naphthenes (N) | 39.9 | 45.0 |
| aromatics (A) | 10.3 | 10.8 |

The aromatization reaction is carried out in a manner identical to the hydroreforming tests described in Example I, with the following conditions:

| | |
|---|---|
| pressure | 10 bars |
| molar ratio hydrogen/hydrocarbons | 5 |
| hourly space velocity | 2 |
| temperature | 520° C. |

The results of the tests carried out in this manner are as follows:

1. for charge A it is noted that the conversion of the paraffins and of the naphthenes is equal to 94.1% and the aromatic selectivity is equal to 45.8%.

2. for charge B, the conversion of (P+N) is equal to 92.4%, the aromatic selectivity being here equal to 53.8%.

This test under pressure confirms therefore that the catalysts in accordance with the invention are very good aromatization catalysts.

For the purpose of simplifying the body of the description of the invention, mention has been made mainly of one of the platinum metals; however, the combinations, within the limits of the quantities indicated do function in the indicated manner and are consequently within the scope of the invention.

The parent application (Ser. No. 690,908) discloses as follows, that the foregoing catalysts lend themselves (in addition to hydroreforming and aromatization) to isomerization of alkylaromatic hydrocarbons.

This isomerization process is similar to hydroreforming. The reactions which it entails also take place in hydroreforming, accompanied by other reactions such as hydrogenation-dehydrogenation, for example, or dehydrocyclization.

The reaction conditions employed in these various processes industrially are not the same. Nor are, as a rule, the catalysts employed in carrying out said reactions necessarily the same.

A great many catalysts are known for the isomerization of alkylaromatic hydrocarbons, for example. Many of them comprise a porous alumina or aluminosilicate carrier on which is deposited a so-called "noble" metal such as platinum, whether or not associated with other metals, among which may be cited iridium, tin, rhenium, lead and germanium. It is also known to associate one or more "non-noble" metals on such a carrier, such as the metals from groups Ib, IIb, Vb or VIb of the periodic table of elements.

The isomerization of alkylaromatic hydrocarbons is an operation that is carried out at a temperature slightly below the temperatures employed in hydroreforming. It is generally carried out below 500° C. and above 350° C., for example, between 430° C. and 480° C., at a pressure on the order of 25 to 35 bars. The space velocity (v/v/hr) of the hydrocarbon charge, measured in the liquid state, usually is in the neighborhood of 1 to 2. The operation is carried out in the presence of hydrogen, the molar ratio of hydrogen to hydrocarbons ranging approximately from 8 to 10.

It is not rare that a good catalyst of one of the processes is an average or poor performer when it is employed in one of the other processes. Under the circumstances, it is remarkable that the catalysts whose general formula is described in the main patent are good catalysts in any of the three processes, hydroreforming, aromatization and isomerization. However, while for the aromatization of hydrocarbons having six or seven carbon atoms no adjustment of the catalytic formula is necessary, in the case of the isomerization of alkylaromatic hydrocarbons, and particularly of those having eight or more carbon atoms, the halogen content must be somewhat higher than the halogen contents used with reforming and aromatization catalysts. Thus, halogen contents ranging approximately from 1 to 2%, based on the total catalyst weight, are preferably employed.

Applicants have found that formulas containing platinum, tin and zirconium are particularly advantageous for the isomerization reaction.

For the usages in accordance with the invention described in this present disclosure, the catalysts may, prior to their utilization, be advantageously subjected to a reduction and possibly a presulfurization; as described in the grandparent disclosure set forth above (see also U.S. Pat. No. 3,974,097).

Example 1

This example illustrates the use of catalysts according to the present invention in the isomerization of an aromatic hydrocarbon having eight carbon atoms, namely, ethylbenzene. Since ethylbenzene is not as much in demand as xylenes, it is advantageous to isomerize it so as to convert it to xylenes.

The catalytic test is conducted under the following conditions:

| | |
|---|---|
| Temperature: | 450° C. |
| Pressure: | 30 bars |
| Space velocity (v/v/hr): | 2 |

-continued

| Ratio of H₂ to charge: | 5 |
|---|---|

The charge is ethylbenzene, which by isomerization gives xylenes and precursors of xylenes such as ethylcyclohexane, dimethylcyclohexanes, methylethylcyclopentanes, etc. The volume of catalyst placed in the reactor is 40 cm³.

The carrier of the catalyst is an alumina identical to the one described above in the grandparent disclosure.

The catalyst comprises 0.37% platinum, 1.35% chlorine, 0.19% tin and 0.15% zirconium. It is tested over several tens of hours. The samples taken from the effluent give information on
the ethylbenzene conversion (that is to say, the percentage of ethylbenzene converted in relation to ethylbenzene introduced), which is indicative of the activity of the catalyst for isomerization;
the selectivity for xylenes, Sx; and
the overall selectivity, St, for xylenes and precursors of xylenes.

Figure 1:
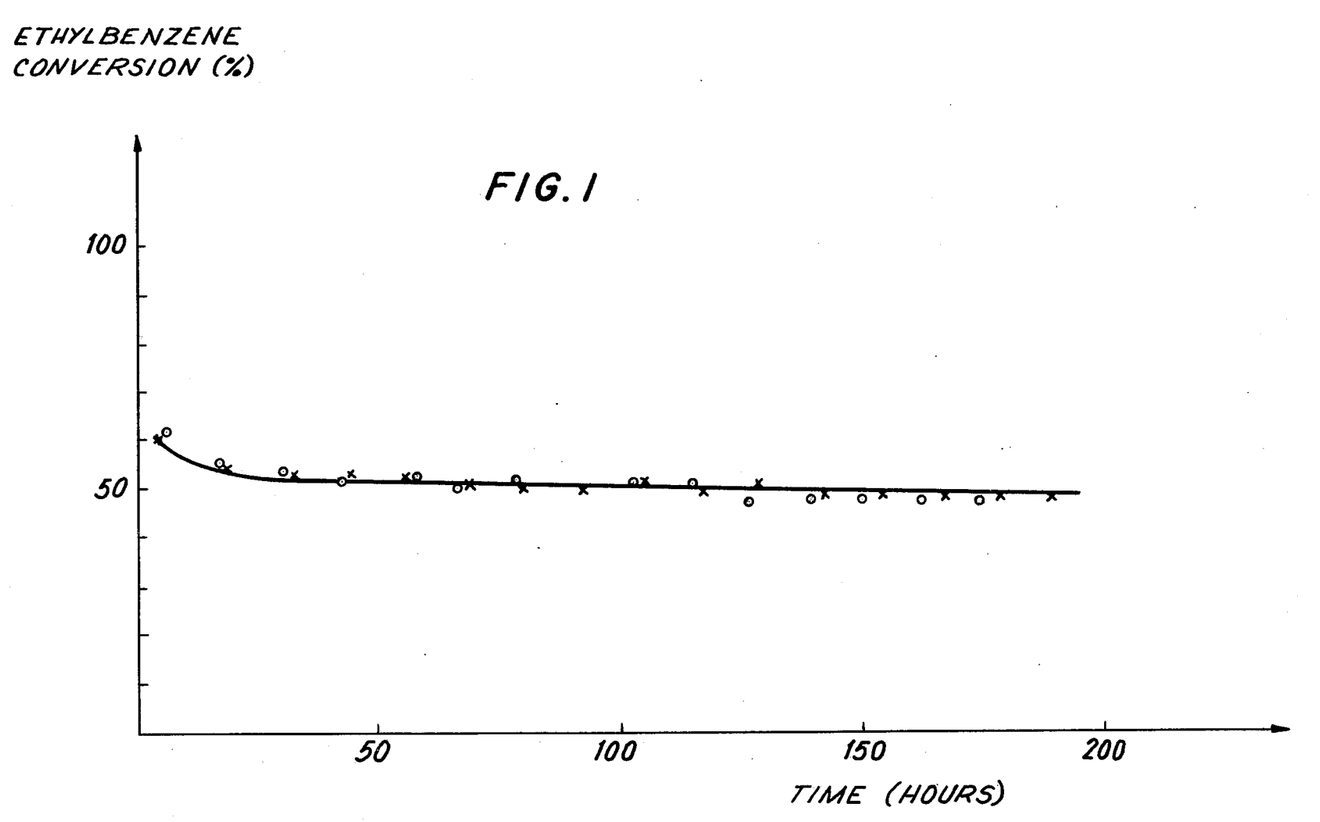
Figure 2:
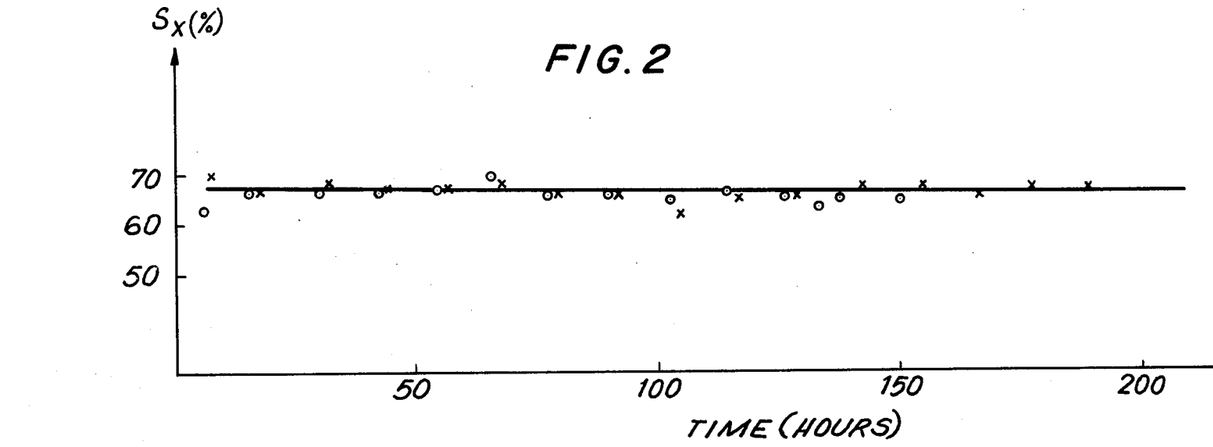
Figure 3:
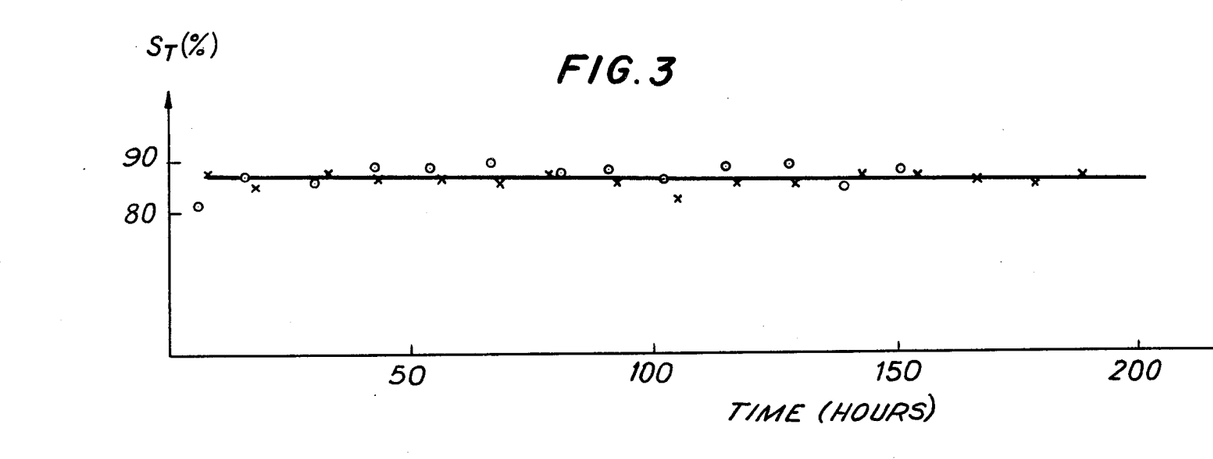

The results of these measurements are presented in the accompanying FIGS. 1, 2 and 3, which illustrate the evolution of the conversion of ethylbenzene and the two selectivities Sx and St (the representative points of these catalysts being marked by a cross, x) as a function of time.

FIG. 1 shows that after a slight decrease in catalyst activity at the start of operation, which is normal, the activity of the catalyst becomes stabilized, ethylbenzene conversion being in the neighborhood of 50%.

FIGS. 2 and 3 show that the catalysts in accordance with the invention are highly selective for xylenes and their precursors, there being practically no variation over the 300 hours of the test. Sx fluctuates between 65 and 70%, St between 85 and 90%.

The catalysts are therefore very good isomerization catalysts.

By way of a comparative example, an identical test was run with a catalyst containing only platinum and chlorine deposited on an identical support, the composition of the catalyst being as follows:
Platinum: 0.35 wt. %
Chlorine: 1.35 wt. %

In FIGS. 1, 2 and 3, the points representative of the behavior of these control catalysts are marked with the symbol o.

When these two catalysts are compared, it is seen that they are substantially equivalent in terms of conversion and selectivity throughout the duration of the test.

However, the applicants have observed that there is a great deal of difference in the amount of carbon deposited on the two catalysts after about 350 hours of operation. In the case of the catalyst containing platinum, tin and zirconium according to the present invention, the rate of carbon deposition is considerably less than 1 wt. % (about 0.8 wt. %) whereas in the case of the conventional catalyst containing only platinum, the rate of carbon deposition is higher than 2 wt. %.

From the industrial point of view, it thus follows that while the catalysts in accordance with the main patent are substantially equivalent to the conventional catalysts in terms of conversion and selectivity during the first few hundred hours of operation, they need to be regenerated less frequently than the conventional catalysts, which is a considerable advantage in the operation of the unit.

Example 2

This example illustrates the utilization of the catalyst, already used in example 1, in the isomerization of hydrocarbon charges containing alkylaromatic hydrocarbons having eight carbon atoms.

Table 1 shows the results of tests performed over six hours on charges whose composition is given in that table.

TABLE 1

| Composition of charge (wt. %) | | | Reaction Conditions | | | | Composition of effluent (wt. %) | | | | | | | |
|---|---|---|---|---|---|---|---|---|---|---|---|---|---|---|
| Ethylbenzene (eb) | Metaxylene (mx) | Orthoxylene (ox) | v/v/hr | Temp. °C. | Relative total pressure (bars) | H₂/HC | Light HC* | Toluene | eb | px | mx | ox | Intermediates HC** | Heavy HC*** |
| 13.50 | 64.50 | 21.40 | 2 | 480 | 35 | 5 | 4.95 | 3.34 | 8.68 | 13.33 | 39.47 | 16.98 | 12.85 | 0.39 |
| 13.50 | 64.50 | 21.40 | 2 | 480 | 25 | 10 | 2.46 | 2.26 | 11.10 | 10.34 | 49.37 | 19.68 | 4.56 | 0.24 |
| 13.50 | 64.50 | 21.40 | 2 | 440 | 25 | 5 | 3.5 | 1.23 | 9.85 | 7.59 | 48.39 | 18.01 | 11.30 | 0.14 |
| 17.45 | 61.30 | 20.15 | 1.5 | 460 | 30 | 7.5 | 3.86 | 2.16 | 11.39 | 10.21 | 44.23 | 17.61 | 10.39 | 0.15 |
| 17.45 | 61.30 | 20.15 | 1.5 | 460 | 30 | 7.5 | 3.09 | 2.38 | 11.65 | 10.38 | 44.74 | 18.15 | 9.28 | 0.34 |
| 19.8 | 59.7 | 19.6 | 1 | 480 | 25 | 10 | 3.69 | 4.14 | 13.81 | 13.59 | 42.83 | 18.46 | 3.24 | 0.24 |
| 19.8 | 59.7 | 19.6 | 1 | 440 | 25 | 5 | 4.41 | 2.25 | 11.95 | 12.72 | 41.40 | 17.38 | 9.5 | 0.38 |
| 19.8 | 59.7 | 19.6 | 2 | 480 | 25 | 5 | 1.90 | 2.78 | 15.85 | 10.23 | 46.75 | 18.96 | 2.76 | 0.75 |
| 19.8 | 59.7 | 19.6 | 2 | 480 | 35 | 10 | 3.43 | 1.30 | 13.74 | 8.64 | 46.36 | 16.54 | 9.92 | 0.08 |

The results presented in this table show that the catalysts in accordance with the main patent have a good isomerizing activity without causing considerable cracking. (Cracking is largely characterized by the quantity of light products obtained).
*"Light HC" means hydrocarbons other than toluene having seven or fewer carbon atoms.
**"Intermediate HC" means the precursors of xylenes.
***"Heavy HC" means hydrocarbons having nine or more carbon atoms, other than precursors of xylenes.

Example 3

In this example, a catalytic test is run with a formula containing:

| 0.38% | platinum |
|---|---|
| 0.19% | tin |
| 0.15% | zirconium |
| 1.81% | chlorine |

The carrier is an alumina identical to the one described in the grandparent disclosure (see also application serial No. 525,675). The principal operating parameters are:

| Temperature: | 450° C. |
|---|---|
| Pressure: | 30 bars |
| Space velocity (v/v/hr): | 2 |
| Molar ratio of | |

-continued

| | |
|---|---|
| hydrogen to hydrocarbons: | 5 |

The hydrocarbon charge which is made to undergo isomerization is a mixed charge having a composition that is variable with time and containing precursors of xylenes and ethylbenzene, these products being the only ones capable of giving, by isomerization, the xylenes sought. The rest of the charge is composed of orthoxylene (about 20 wt. %) and metaxylene (about 60 wt. %).

Table 2 presents the results of this test, in which about 20 ppm of water and 10 ppm of chlorine were injected with the charge so as to maintain the chlorine content of the catalyst with time.

It is apparent from this table that the performance of this formula is very good.

Applicants have discovered an improvement on the isomerization process of the parent disclosure, just described.

A preferred embodiment of said improvement in the process for the isomerization of a charge of alkylaromatic hydrocarbons, comprises contacting, in at least two successive stages, said hydrocarbon charge, hydrogen and, in at least one of said stages, a catalyst described in the grandparent disclosure.

For greater clarity of the outline of the improvement invention, the latter will be described with regard to the successive stages, each of which makes use of but one reactor. However, this is not intended as a limitation as the process may be practiced in two successive stages each comprising more than two reactors which in each stage may be operated in parallel or in series. Similarly, while only two successive stages are assumed, it will be understood that the process in accordance with the improvement invention may be practiced with a larger number of stages.

The conditions of temperature and pressure may be identical in the two successive stages. However, the applicants have found that very good results are obtained when the conditions are not the same in both stages.

In each of these two stages, the conditions may vary over the following ranges:

Molar ratio of hydrogen to hydrocarbons:
Between 3 and 15, and preferably approximately between 8 and 10.

Temperature: Below approximately 550° C. and above approximately 250° C., as a rule.

Pressure: Approximately between 3 and 40 bars.

The overall space velocity, that is to say, the space velocity referred to the total volume of catalyst contained in all reactors, may range from 0.4 to 4, and advantageously from 1 to 2.5.

Table i which follows gives the conditions under which it is advantageous, in the opinion of the applicants, to operate each stage, in the case where only two stages are employed.

Table i

| | Operating conditions 1st Stage | Operating conditions 2nd Stage |
|---|---|---|
| Partial space velocity (v/v/h) | Between 1 and 4 | Between 1 and 6 |
| Molar ratio of hydrogen to hydrocarbons | 3 to 15 | 3 to 15 |
| Temperature | 100 to 450° C.; preferably 240 to 450° C. | 300 to 550° C.; preferably 350 to 500° C. |
| Pressure | 10 to 40 bars; preferably 20 to 35 bars | 3 to 30 bars; preferably 10 to 25 bars |

TABLE 2

| | Composition of charge | | | Partial composition of effluent (wt. %)*** | | | |
|---|---|---|---|---|---|---|---|
| Age of catalyst (hours) | Intermediates % | Ethylbenzene % | Ethylbenzene Conversion | C7− fraction* | C9+ fraction** | Aromatics with C8 | Paraxylene |
| 284 | 4.96 | 17.68 | 41.9 | 5.35 | 1.13 | 84.7 | 17.0 |
| 292 | 4.96 | 17.68 | 38.7 | 4.84 | 0.82 | 86.2 | 16.2 |
| 356 | 0 | 22.45 | 43.7 | 4.95 | 1.02 | 88.0 | 15.83 |
| 380 | 7.35 | 16.77 | 35.4 | 5.78 | 1.02 | 83.96 | 16.17 |
| 388 | 7.35 | 16.77 | 36.7 | 5.64 | 1.08 | 84.88 | 15.62 |
| 404 | 0 | 19.11 | 36.6 | 4.64 | 1.02 | 87.4 | 17.97 |
| 412 | 0 | 19.11 | 37.2 | 3.74 | 0.90 | 89.2 | 17.64 |
| 493 h 30 | 0 | 22.45 | 40.3 | 4.63 | 0.79 | 88.65 | 16.3 |
| 501 h 30 | 0 | 22.45 | 37.55 | 5.57 | 1.16 | 87.3 | 16.0 |
| 517 h 30 | 9.75 | 16.25 | 37.85 | 5.51 | 1.15 | 83.97 | 16.73 |
| 524 h 30 | 9.75 | 16.25 | 32.61 | 6.01 | 0.92 | 83.55 | 16.10 |
| 540 h 30 | 0 | 22.45 | 40.44 | 4.51 | 1.18 | 88.8 | 16.96 |
| 549 h 30 | 0 | 22.45 | 39.55 | 4.74 | 1.17 | 88.3 | 16.0 |

*C7− fraction = formed of hydrocarbons having seven or fewer carbons
**C9+ fraction = formed of hydrocarbons having nine or more carbons
***The rest of the effluent is formed of naphthenes and paraffins having eight carbons The applicants have found that the performance of the catalysts according to the grandparent disclosure in the isomerization reaction of alkylaromatic hydrocarbons is improved when the process in accordance with the present improvement invention is practiced under the conditions set forth above.

The two-stage process lends itself particularly well to the treatment, under the conditions set forth above, of hydrocarbon charges containing mostly hydrocarbons having eight carbon atoms with a view to augmenting the production of paraxylenes by conversion of the other hydrocarbons contained in the charge. The process is particularly well suited to charges containing approximately from 5 to 50% of ethylbenzene.

The catalysts employed in the two stages may have identical or different compositions. The halogen (generally chlorine) content of the catalyst used in the first stage is higher than that of the second stage, provided that the conditions of the two stages are as specified in the above Table i. The equilibrium between water (contained in the charge fed to the reactor) and chlorine actually is a function of said conditions.

Apart from the chlorine content, the composition of the catalysts may vary due to the nature of the active metals or promoters deposited on the carrier. Thus, when the isomerization process is practiced in only two stages, for example, a catalytic formulation containing platinum as the only metal may be used in the first reactor, and a catalytic formulation in the second reactor according to the grandparent disclosure. The following catalyst combinations may also be used:
- in the first reactor, a catalyst in accordance with French patent 2,031,984 (see also U.S. patent 3,700,588) containing a platinum-group metal and tin as active metals, or a catalyst containing at least one platinum-group metal on a refractory oxide carrier, possibly with one or more promoters designed to improve a given catalyst property, such as service life, activity, stability, inhibition of cracking tendencies, etc.
- in the second reactor, a catalyst according to the grandfather disclosure above.

The deployment of the different formulations used in the two stages may be as desired. Thus, the catalyst according to the grandfather disclosure may be employed in the first stage or in the second stage or in all stages. However, the applicants have found that it is more advantageous to deply said catalyst in particular in the second stage when only two stages are used in practicing the isomerization process, and has obtained good results with a platinum/alumina formulation in the first stage and a platinum-tin-zirconium/alumina formulation in the second stage. The platinum/alumina formulation of the first reactor may, without greatly affecting the results, be replaced with a platinum-tin formulation, as has been pointed out earlier.

The halogen (generally chlorine) content of the catalytic formulations used in the various stages will vary from one stage to the next owing to the different operating conditions of these stages.

Thus, the halogen content will preferably be comprised between 1 and 2% in each stage. However, the halogen content of the catalysts of the first stage will be higher than that of the second stage, the difference ranging approximately from 0.05 to 0.50%, based on the weight of the catalyst.

As is known, the purpose of the halogen is to impart a certain acidity to the refractory oxide carrier. Other elements having this property may likewise be added to the different catalytic formulations used in each stage. Thus, the applicants have successfully used additions of silicon at the rate of about 0.1 to 2%, based on the total weight of the catalyst, to said catalytic formulations.

The examples which follow are illustrative of the invention, both in the case where the catalysts according to the grandfather disclosure are used in both stages and in the case where said catalysts are used only in the last stage of the process. These examples are nonlimitative in character.

Example a

One achieves, as indicated earlier, the isomerization of a charge of alkylaromatic hydrocarbons of the following composition:

| Toluene: | 1.07% | |
|---|---|---|
| Ethylbenzene: | 27.45% | |
| Paraxylene: | 1.44% | ⎫ |
| Metaxylene: | 68.67% | ⎬ 71.42% |
| Orthoxylene: | 1.31% | ⎭ |

It is sought to obtain a maximum paraxylene yield through this reaction.

The following catalytic formulations are used:

| Catalyst According To The Grandfather Disclosure (A) | |
|---|---|
| Platinum: | 0.35 wt. % |
| Tin: | 0.20 wt. % |
| Zirconium: | 0.15 wt. % |
| Control Catalyst (B) | |
| Platinum: | 0.35 wt. % |

The carriers of these catalysts are aluminas of conventional properties:
Specific surface: 185 m$^2$/g
Pore volume: 0.48 cm$^3$/g
Average pore radius: 40 Å

The chlorine content of these catalysts, set forth in Table ii below, is maintained substantially constant by injection into the undehydrated charge of alkylaromatic hydrocarbons of 184 ppm of chlorine in the form of dichloropropane so as to compensate for dechlorination due to the moisture in the charge.

A number of tests were run whose conditions are reported in Table ii.

Table ii

| Test No. | 1 | | 2 | 3 | 4 | 5 | 6 | 7 | | 8 | 9 | 10 | 11 | 12 |
|---|---|---|---|---|---|---|---|---|---|---|---|---|---|---|
| Catalyst used | A | | A | A | A | A | A | B | | B | B | B | B | B |
| Number of stages | 2 | | 1 | 1 | 1 | 1 | 1 | 2 | | 1 | 1 | 1 | 1 | 1 |
| | 1st stage | 2nd stage | | | | | | 1st stage | 2nd stage | | | | | |
| Temperature, °C. | 350 | 475 | 475 | 475 | 420** | 420** | 447.5 | 350 | 475 | 475 | 475 | 420** | 420** | 447.5 |
| Pressure, bars | 30 | 15 | 30 | 15 | 30 | 15 | 22.5 | 30 | 15 | 30 | 15 | 30 | 15 | 22.5 |
| Overall space velocity (v/v/h)* | 1.25 | | 1.25 | 1.25 | 1.25 | 1.25 | 1.25 | 1.25 | | 1.25 | 1.25 | 1.25 | 1.25 | 1.25 |
| Molar ratio hydrogen/charge | 10 | | 10 | 10 | 10 | 10 | 10 | 10 | | 10 | 10 | 10 | 10 | 10 |
| Chlorine content of catalyst | 1.83 | 1.59 | 1.59 | 1.59 | 1.59 | 1.59 | 1.59 | 1.81 | 1.56 | 1.45 | 1.45 | 1.45 | 1.45 | 1.45 |
| Catalyst volume, cm$^3$ | 17 | 10 | 27 | 27 | 27 | 27 | 17 | 10 | 27 | 27 | 27 | 27 | 27 | 27 |

*The overall space velocity (v/v/h) is the space velocity referred to the total catalyst volume.
**The temperature of 420° C. was chosen in place of 350° C. because at the latter temperature the major portion of the effluent at between 15 and 30 bars is not composed of aromatics for reasons of thermodynamic equilibrium. For a valid comparison, it is therefore preferable to choose 420° C.

The results of these tests are presented in Table iii. Shown in that table are:
The yield in weight percent of the different products in the effluent;
The total yield R$_1$, in percent, of hydrocarbons having eight carbon atoms;
the ratio R$_2$ = xylenes in the charge/xylenes in the effluent, and
the ethylbenzene conversion C$_{EB}$ in percent.

Table iii

| Test No. | 1 | 2 | 3 | 4 | 5 | 6 | 7 | 8 | 9 | 10 | 11 | 12 |
|---|---|---|---|---|---|---|---|---|---|---|---|---|
| Total yield, wt. % | 97 | 97 | 97 | 97 | 97 | 97 | 93 | 92.3 | 93.3 | 97 | 97 | 97 |
| Light hydrocarbons* | 0.91 | 4.99 | 1.08 | 2.28 | 0.84 | 2.11 | 3.82 | 10.26 | 2.73 | 2.80 | 0.70 | 1.86 |
| Benzene | 0.66 | 2.79 | 1.54 | — | — | 1.86 | 1.30 | — | 2.80 | — | — | — |
| Toluene | 4.04 | 3.25 | 4.70 | 1.14 | 1.27 | 1.96 | 7.93 | 9.15 | 11.67 | 1.64 | 1.99 | 3.00 |
| C8 paraffins** | 2.04 | 26.78 | 2.82 | 70.66 | 22.89 | 23.47 | 4.52 | 11.13 | 1.88 | 48.67 | 13.61 | 16.19 |
| Ethylbenzene | 12.63 | 5.22 | 15.66 | 1.67 | 10.58 | 6.60 | 9.87 | 6.32 | 13.81 | 4.14 | 16.14 | 12.08 |
| Paraxylene | 18.38 | 12.96 | 16.60 | 5.19 | 13.84 | 14.67 | 15.55 | 12.93 | 12.96 | 9.53 | 11.20 | 14.11 |
| Metaxylene | 39.97 | 28.38 | 38.94 | 11.30 | 35.34 | 32.38 | 32.93 | 28.96 | 35.45 | 21.47 | 44 — | 36.73 |
| Orthoxylene | 17.88 | 12.16 | 15.09 | 4.64 | 11.98 | 13.58 | 16.51 | 12.45 | 11.49 | 8.56 | 9.20 | 12.80 |
| Heavy hydrocarbons*** | 0.48 | 0.48 | 0.59 | 0.12 | 0.24 | 0.37 | 0.57 | 0.99 | 0.50 | 0.21 | 0.14 | 0.22 |
| $R_1$ | 88.9 | 58.7 | 86.3 | 22.8 | 71.7 | 67.2 | 74.9 | 60.7 | 73.7 | 43.7 | 80.5 | 75.7 |
| $R_2$ | 1.07 | 0.75 | 0.99 | 0.29 | 0.86 | 0.85 | 0.91 | 0.76 | 0.84 | 0.55 | 0.90 | 0.89 |
| $C_{EB}$ | 54 | 81 | 42.9 | 93.9 | 61.5 | 76.0 | 64 | 76.8 | 49.4 | 84.8 | 40.9 | 55.7 |

*Light hydrocarbons = Hydrocarbons having seven or fewer carbon atoms, except benzene and toluene
**C8 paraffins = Paraffinic and cycloparaffinic hydrocarbons having eight carbon atoms
***Heavy hydrocarbons = Hydrocarbons having nine or more carbon atoms The results obtained and summarized in Table iii call for a few explanatory notes:

(1) In a single stage, the best result with the Pt-Sn-Zr formulation was obtained at 15 bars and 475° C. (Test No. 3; see the paraxylene yield, the $R_2$ ratio and the $R_1$ yield.)

(2) When tests No. 3 and No. 1 are compared, it is seen that in two stages
the total yield $R_1$ is greater,
the $R_2$ ratio is also higher, and
the paraxylene yield is higher.

It is therefore more advantageous to operate in two stages, rather than in just one, to augment paraxylene production.

(3) In a single stage, the best result with the Pt formulation was obtained at 22.5 bars and 447.5° C. (Test No. 12; see the paraxylene yield.)

(4) When tests No. 12 and No. 7 are compared, it is seen that it is more advantageous to operate in two stages (test No. 7) as this permits increasing the paraxylene yield. However, paraxylene production is less than with the Pt-Sn-Zr formulations according to the grandfather disclosure, and the advantage gained by working in two stages instead of one is greater when the Pt-Sn-Zr formulations are used.

Example b

In this example, a hydrocarbon charge of practically constant composition consisting mainly of metaxylene and ethylbenzene is isomerized. The isomerization is carried out in accordance with the invention in two reactors under the following conditions:

First reactor

Pressure: 20 bars.
Temperature: 280° C.
25 cm³ of catalyst containing 0.35 wt. % platinum and 1.6% of chlorine on alumina.

Second reactor

Pressure: 15 bars.
Temperature: Variable (between 490 and 530° C.).
15 cm³ of catalyst whose composition varies from one test to another. (Tests A to F; see Table iv below.) Alumina carrier.

The overall space velocity is 1.5, and the molar ratio of hydrogen to hydrocarbon is 7.5. Dichloropropane is added to the hydrocarbon charge at the rate of 180 ppm per 200 ppm of water present in the charge.

At the start of the reaction, the catalysts contained in the reactors are subjected to a reducing treatment with hydrogen (at 20 bars) for two hours at 500° C.

The catalysts used in the second reactor are specified in Table iv which follows.

Table iv

| Test Catalyst | A (Control) | B (Control) | C | D | E | F |
|---|---|---|---|---|---|---|
| Platinum, wt. % | 0.35 | 0.35 | 0.34 | 0.38 | 0.37 | 0.36 |
| Tin, wt. % | — | 0.20 | 0.21 | 0.22 | 0.22 | 0.20 |
| Zirconium, wt. % | — | — | 0.15 | 0.14 | 0.15 | 0.79 |
| Chlorine, wt. % | 1.66 | 1.69 | 1.80 | 1.68 | 1.73 | 1.67 |
| Composition of charge, wt. %: | | | | | | |
| Toluene | 0 | 0 | 0.03 | 0.07 | 0.18 | 0 |
| Ethylbenzene | 27.56 | 27.26 | 27.45 | 27.38 | 27.47 | 27.56 |
| Paraxylene | 2.30 | 2.11 | 2.09 | 2.10 | 2.29 | 2.30 |
| Metaxylene | 68.07 | 68.82 | 62.42 | 62.64 | 63.91 | 68.07 |
| Orthoxylene | 2.07 | 1.81 | 8.01 | 7.81 | 6.15 | 2.07 |
| Total xylenes | 72.44 | 72.74 | 72.52 | 72.55 | 72.35 | 72.44 |

The results obtained in tests A to F are presented in Tables v to x which follow. Shown in particular are the ratio R = paraxylene in effluent/paraxylene in effluent plus losses, the losses being constituted by benzene, toluene, light hydrocarbons (having fewer than seven carbon atoms, except benzene and toluene), and heavy hydrocarbons (having nine or more carbon atoms), R represents the paraxylene yield in relation to the fresh charge if the hydrocarbons having eight carbon atoms are recycled after separation of the paraxylene and the losses. $C_{EB}$ is the ethylbenzene conversion.

Table V

| | Test A | | | | |
|---|---|---|---|---|---|
| Temperature, ° C. | 490 | 500 | 510 | 520 | 530 |
| Yield by weight: | | | | | |
| Light hydrocarbons | 0.91 | 1.16 | 1.05 | 1.43 | 1.74 |
| Benzene | 0.43 | 1.05 | 1.11 | 1.29 | 1.52 |
| Toluene | 1.80 | 2.28 | 3.16 | 3.70 | 4.24 |
| Saturated hydrocarbons having 8 carbon atoms | 7.11 | 4.44 | 3.10 | 2.17 | 1.42 |
| Ethylbenzene | 15.60 | 15.58 | 16.58 | 15.25 | 16.01 |
| Paraxylene | 16.73 | 17.05 | 16.43 | 16.81 | 16.32 |
| Metaxylene | 39.14 | 39.38 | 39.28 | 38.30 | 37.78 |
| Orthoxylene | 14.96 | 15.46 | 14.83 | 15.67 | 15.04 |
| Heavy hydrocarbons | 0.31 | 0.43 | 0.66 | 0.90 | 0.70 |
| R | 0.829 | 0.776 | 0.733 | 0.697 | 0.666 |
| $C_{EB}$ | 43.4 | 43.5 | 39.8 | 44.6 | 41.9 |

Table vi

| | Test B | | | | |
|---|---|---|---|---|---|
| Temperature, °C. | 490 | 500 | 510 | 520 | 530 |
| Yield by weight: | | | | | |
| Light hydrocarbons | 0.90 | 0.50 | 0.85 | 0.76 | 0.93 |
| Benzene | 0.75 | 0.42 | 0.80 | 0.87 | 1.11 |
| Toluene | 0.94 | 1.17 | 1.56 | 2.07 | 2.67 |
| Saturated hydrocarbons having 8 carbon atoms | 4.32 | 3.57 | 2.20 | 1.20 | 0.74 |
| Ethylbenzene | 15.37 | 16.04 | 16.20 | 15.93 | 16.31 |
| Paraxylene | 17.62 | 17.52 | 17.62 | 17.80 | 17.60 |
| Metaxylene | 40.38 | 40.64 | 40.47 | 40.30 | 39.78 |
| Orthoxylene | 16.88 | 16.78 | 16.88 | 17.28 | 17.08 |
| Heavy hydrocarbons | 0.22 | 0.34 | 0.42 | 0.81 | 0.80 |
| R | 0.879 | 0.878 | 0.846 | 0.798 | 0.762 |
| $C_{EB}$ | 43.6 | 41.2 | 40.6 | 41.6 | 40.2 |

Table vii

| | Test C | | | |
|---|---|---|---|---|
| Temperature, °C. | 500 | 510 | 520 | 530 |
| Yield by weight: | | | | |
| Light hydrocarbons | 0.58 | 0.68 | 0.77 | 0.98 |
| Benzene | — | 0.45 | 0.61 | 1.06 |
| Toluene | 0.85 | 1.15 | 1.59 | 2.12 |
| Saturated hydrocarbons having 8 carbon atoms | 7.62 | 3.98 | 2.62 | 2.58 |
| Ethylbenzene | 16.23 | 17.02 | 16.80 | 16.56 |
| Paraxylene | 16.46 | 16.51 | 16.62 | 16.79 |
| Metaxylene | 39.20 | 40.18 | 40.30 | 39.14 |
| Orthoxylene | 15.69 | 16.78 | 17.29 | 17.01 |
| Heavy hydrocarbons | 0.35 | 0.25 | 0.40 | 0.74 |
| R | 0.902 | 0.867 | 0.832 | 0.774 |
| $C_{EB}$ | 40.9 | 38.0 | 38.8 | 39.7 |

Table viii

| | Test D | | | | |
|---|---|---|---|---|---|
| Temperature, °C. | 490 | 500 | 510 | 520 | 530 |
| Yield by weight: | | | | | |
| Light hydrocarbons | 0.51 | 0.76 | 0.64 | 0.57 | 0.84 |
| Benzene | — | — | 0.45 | 0.78 | 0.70 |
| Toluene | 0.91 | 1.13 | 1.41 | 1.41 | 1.78 |
| Saturated hydrocarbons having 8 carbon atoms | 8.69 | 6.37 | 3.78 | 2.92 | 2.33 |
| Ethylbenzene | 15.54 | 16.02 | 17.49 | 17.76 | 17.67 |
| Paraxylene | 16.31 | 16.49 | 16.43 | 16.51 | 16.73 |
| Metaxylene | 38.35 | 38.95 | 39.60 | 39.72 | 39.41 |
| Orthoxylene | 16.49 | 16.95 | 16.92 | 16.98 | 17.14 |
| Heavy hydrocarbons | 0.23 | 0.35 | 0.29 | 0.35 | 0.40 |
| R | 0.908 | 0.881 | 0.855 | 0.842 | 0.818 |
| $C_{EB}$ | 43.2 | 41.5 | 36.6 | 35.1 | 35.4 |

Table ix

| | Test E | | | | |
|---|---|---|---|---|---|
| Temperature, °C. | 490 | 500 | 510 | 520 | 530 |
| Yield by weight: | | | | | |
| Light hydrocarbons | 0.45 | 0.63 | 0.86 | 0.85 | 0.96 |
| Benzene | — | — | 0.46 | 0.94 | 1.09 |
| Toluene | 1.02 | 1.26 | 1.59 | 2.28 | 2.73 |
| Saturated hydrocarbons having 8 carbon atoms | 8.57 | 5.82 | 4.20 | 2.65 | 1.88 |
| Ethylbenzene | 15.68 | 16.13 | 16.41 | 15.59 | 15.65 |
| Paraxylene | 16.32 | 16.74 | 16.84 | 17.33 | 17.23 |
| Metaxylene | 38.51 | 39.20 | 39.33 | 39.33 | 39.09 |
| Orthoxylene | 16.28 | 16.85 | 17.01 | 17.50 | 17.45 |
| Heavy hydrocarbons | 0.18 | 0.39 | 0.30 | 0.54 | 0.74 |
| R | 0.908 | 0.880 | 0.840 | 0.790 | 0.757 |
| $C_{EB}$ | 42.9 | 41.3 | 40.3 | 43.2 | 43.0 |

Table x

| | Test F | | | | |
|---|---|---|---|---|---|
| Temperature, °C. | 490 | 500 | 510 | 520 | 530 |
| Yield by weight: | | | | | |
| Light hydrocarbons | 0.56 | 0.94 | 0.93 | 0.86 | 0.92 |
| Benzene | — | 0.30 | 0.67 | 0.76 | 0.92 |
| Toluene | 0.96 | 1.25 | 1.70 | 1.98 | 2.54 |
| Saturated hydrocarbons having 8 carbon atoms | 6.08 | 4.43 | 2.53 | 1.71 | 0.99 |
| Ethylbenzene | 15.56 | 15.83 | 16.20 | 16.18 | 15.95 |
| Paraxylene | 17.32 | 17.44 | 17.58 | 17.68 | 17.68 |
| Metaxylene | 39.14 | 39.29 | 39.64 | 39.86 | 39.41 |
| Orthoxylene | 16.99 | 17.27 | 17.48 | 17.49 | 17.63 |
| Heavy hydrocarbons | 0.38 | 0.24 | 0.27 | 0.49 | 0.93 |
| R | 0.901 | 0.865 | 0.831 | 0.812 | 0.769 |
| $C_{EB}$ | 43.5 | 42.6 | 41.2 | 41.3 | 42.1 |

In the light of the results presented in these tables, it may be conclued that the process in accordance with the invention is very effective in the isomerization of aromatic C8's. In particular, it is very advantageous in relation to a process using only platinum catalysts. Comparison with a platinum-tin formulation used in the second reactor points up the advantage of platinum-tin-zirconium formulations as used in tests C and D. The resuls of tests E, F and B are substantially the same.

Figure 4:
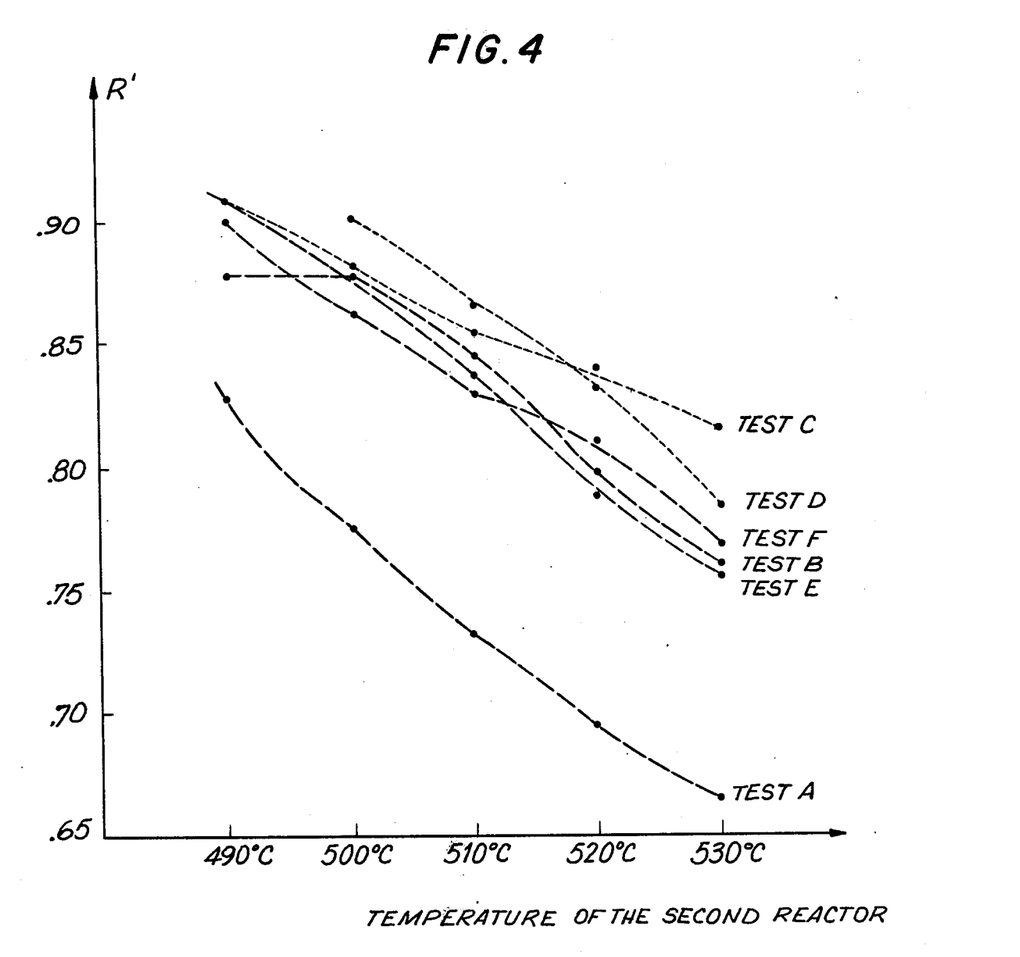

For greater clarity of this comparison, the accompanying FIG. 4 shows the curves giving the values of the ratio R for each catalyst combination used in tests A to F as a function of temperature.

We claim:

1. A process of reforming a hydrocarbon charge comprising placing said hydrocarbon charge, hydrogen, and a catalyst under reforming conditions, said catalyst comprising a refractory inorganic oxide support having acid sites, having between about 0.4 and 2% of halogen present in combined form with other catalyst components, and consisting essentially of the following on said support;
   (a) about 0.02 to 2% of at least one platinummetal ingredient,
   (b) about 0.02 to 2% of at least one additional zirconium or titanium ingredient, and
   (c) about 0.02 to 2% of a tin ingredient;
   said weight percentages being calculated with respect to the respective elemental forms of said components and based on the total weight of the catalyst.

2. A process according to claim 1, wherein said ingredients are only of tin, of platinum and of zirconium, the support is an alumina whose specific surface is between 100 and 350 m²/g and whose specific pore volume is of more than 0.1 cm³/g, and said halogen is chlorine.

3. A process according to claim 1, comprising first reducing said catalyst by hydrogen.

4. A process according to claim 2, comprising first subjecting said catalyst to reduction by hydrogen and presulfurizing by hydrogen sulfide.

5. A process of aromatizing a hydrocarbon charge comprising placing said hydrocarbon charge, hydrogen, and a catalyst under aromatizing conditions, said catalyst comprising a refractory inorganic oxide support having acid sites, having between about 0.4 and 2% of halogen present in combined form with other catalyst components, and consisting essentially of the following on said support:
   (a) about 0.02 to 2% of at least one platinum-metal ingredient,
   (b) about 0.02 to 2% of at least one additional zirconium or titanium ingredient, and
   (c) about 0.02 to 2% of a tin ingredient;

said weight percentages being calculated with respect to the respective elemental forms of said components and based on the total weight of the catalyst.

6. A process according to claim 5, wherein said ingredients are only of tin, of platinum and of zirconium, the support is an alumina whose specific surface is between 100 and 350 m²/g and whose specific pore volume is of more than 0.1 cm³/g, and said halogen is chlorine.

7. A process according to claim 5, comprising first reducing said catalyst by hydrogen.

8. A process according to claim 6, comprising first subjecting said catalyst to reduction by hydrogen and presulfurizing by hydrogen sulfide.

9. A process for isomerization of charge of alkylaromatic hydrocarbons which comprises contacting, under conditions of isomerization, said hydrocarbon charge, hydrogen and a catalyst comprising a refractory inorganic oxide support having acid sites, having between about 0.4 and 2% of halogen present in combined form with other catalyst components, and consisting essentially of the following on said support:
 (a) about 0.02 to 2% of at least one platinum-metal ingredient;
 (b) about 0.02 to 2% of at least one additional zirconium or titanium ingredient, and
 (c) about 0.02 to 2% of a tin ingredient;
said weight percentges being calculated with respect to the respective elemental forms of said components and based on the total weight of the catalyst.

10. A process according to claim 9, wherein said ingredients are only of tin, of platinum and of zirconium, the support is an alumina whose specific surface is between 100 and 350 m²/g and whose specific pore volume is of more than 0.1 cm³/g, and said halogen is chlorine.

11. A process according to claim 9, which comprises
 (a) reducing said catalyst with hydrogen before contacting said hydrocarbon charge with the catalyst so prepared, under isomerization conditions 12. A process according to claim 10, which comprises reducing said catalyst with hydrogen befre contacting said hydrocarbon charge with the catalyst so prepared, under isomerization conditions.

13. A process according to claim 12, further comprising a presulfurization of the catalyst with sulfurized hydrogen.

14. An isomerization process according to claim 9, further comprising said catalyst consisting of from 1 to 2% by weight of halogen.

15. An isomerization process according to claim 12, further comprising said catalyst consisting of from 1 to 2% by weight of chlorine.

16. A process according to claim 14, wherein said halogen is chlorine.

17. A process according to claim 9, wherein said hydrocarbons are alkylaromatic hydrocarbons and have eight carbon atoms.

18. A process according to claim 15, wherein said hydrocarbons are alkylaromatic hydrocarbons and have eight carbon atoms.

19. In a process for the isomerization of alkylaromatic hydrocarbons comprising the contacting of the hydrocarbon charge, hydrogen, and a catalyst the improvement to said process, comprising practicing said isomerization in at least two successive stages, said contacting taking place in at least one of said stages with a specific catalyst comprising a refractory inorganic oxide support having acid sites, having between about 0.4 and 2% of halogen present in combined form with other catalyst components, and consisting essentially of the following on said support:
 (a) about 0.02 to 2% of at least one platinum-metal ingredient,
 (b) about 0.02 to 2% of at least one additional zirconium or titanium ingredient, and
 (c) about 0.02 to 2% of a tin ingredient;
said weight percentages being calculated with respect to the respective elementl forms of said components and based on the total weight of the catalyst.

20. Process in accordance with claim 19, wherein the operating conditions of the stages are as follows:
 (a) Pressure: Comprised between 3 and 40 bars,
 (b) Temperature: Comprised between 250° and 550° C.,
 (c) Overall space velocity (v/v/h), measured in the liquid state: Comprised between 0.5 and 4,
 (d) Molar ratio of hydrogen to hydrocarbons: Comprised between 3 and 15.

21. Process according to claim 20, wherein v/v/h is between 1 and 2.5.

22. Process in accordance with claim 19, wherein the number of stages is two and the operating conditions of the first stage are as follows:
 (a) Pressure: 10 to 40 bars,
 (b) Temperature: 100° to 450° C.,
 (c) Space velocity: 1 to 4,
 (d) Molar ratio of hydrogen to hydrocarbons: 3 to 15.

23. Process in accordance with claim 19, wherein the number of stages is two and the operating conditions of the first stage are as follows:
 (a) Pressure: 20 to 35 bars,
 (b) Temperature: 250° to 450° C.,
 (c) Space velocity: 1 to 4.
 (d) Molar ratio of hydrogen to hydrocarbons: 3 to 15.

24. Process in accordance with claim 19, wherein the number of stages is two and the operating conditions of the second stage are as follows:
 (a) Pressure: 3 to 30 bars,
 (b) Temperature: 30° to 550° C.
 (c) Space velocity: 1 to 6,
 (d) Molar ratio of hydrogen to hydrocarbons: 3 to 15.

25. Process in accordance with claim 22, wherein the number of stages is two and the operating conditions of the second stage are as follows:
 (a) Pressure: 3 to 30 bars,
 (b) Temperature: 30° to 550° C.,
 (c) Space velocity: 1 to 6
 (d) Molar ratio of hydrogen to hydrocarbons: 3 to 15.

26. Process in accordance with claim 19, wherein the number of stages is two and the operating conditions of the second stage are as follows:
 (a) Pressure 10 to 25 bars,
 (b) Temperature: 350° to 500° C.,
 (c) Space velocity: 1 to 6,
 (d) Molar ratio of hydrogen to hydrocarbons: 3 to 15.

27. Process in accordance with claim 23, wherein the number of stages is two and the operating conditions of the second stage are as follows:
 (a) Pressure: 10 to 25 bars,
 (b) Temperature: 250° to 500° C.,
 (c) Space velocity: 1 to 6,
 (d) Molar ratio of hydrogen to hydrocarbons: 3 to 15.

28. Process in accordance with claim 19, wherein operating conditions of the two stages are identical.

29. Process in accordance with claim 20, wherein the operating conditions of the two stages are identical.

30. Process in accordance with claim 19, wherein the operating conditions of the two stages differ as follows:

|  | First Stage | Second Stage |
|---|---|---|
| Partial space velocity (v/v/h): | Between 1 and 4 | Between 1 and 6 |
| Molar ratio of hydrogen to hydrocarbons: | 3 to 15 | 3 to 15 |
| Temperature: | 100° to 450° C. | 300° to 550° C. |
| Pressure: | 10 to 40 bars | 3 to 30 bars. |

31. Process in accordance with claim 25, wherein the operating conditions of the two stages differ as follows:

|  | First Stage | Second Stage |
|---|---|---|
| Partial space velocity (v/v/h): | Between 1 and 4 | Between 1 and 6 |
| Molar ratio of hydrogen to hydrocarbons: | 3 to 15 | 3 to 15 |
| Temperature: | 100° to 450° C. | 300° to 550° C. |
| Pressure: | 10 to 40 bars | 3 to 30 bars. |

32. Process in accordance woth claim 27, wherein the operating conditions of the two stages differ as follows:

|  | First Stage | Second Stage |
|---|---|---|
| Partial space velocity (v/v/h): | Between 1 and 4 | Between 1 and 6 |
| Molar ratio of hydrogen to hydrocarbons: | 100° to 450° C. | 300° to 550° C. |
| Pressure: | 10 to 40 bars | 3 to 30 bars. |

33. Process in accordance with claim 28, wherein the catalysts used in said successive stages are identical.

34. Process in accordance with claim 29, wherein the catalysts used in said successive stages are identical.

35. Process in accordance with claim 30, wherein the catalysts used in said successive stages are identical.

36. Process in accordance with claim 31, wherein the catalysts used in said successive stages are identical.

37. Process in accordance with claim 28, wherein the catalysts used in the successive stages are different in their metal ingredient composition.

38. Process in accordance with claim 29, wherein the catalysts used in the successive stages are different in their metal ingredient composition.

39. Process in accordance with claim 30, wherein the catalysts used in the successive stages are different in their metal ingredient composition.

40. Process in accordance with claim 31 wherein the catalysts used in the successive stages are different in their metal ingredient composition.

41. Process in accordance with claim 19, wherein the halogen content of the catalysts varies from one stage to the next, the first stage using a catalyst containing approximately from 0.05% more halogen, based on the total weight of the catalysts, than the second stage.

42. Process in accordance with claim 20, wherein the halogen content of the catalysts varies from one stage to the next, the first stage using a catalyst containing approximately from 0.05 to 0.50% more halogen, based on the total weight of the catalysts, than the second stage.

43. Process in accordance with claim 25, wherein the halogen content of the catalysts varies from one stage to the next, the first stage using a catalyst containing approximately from 0.05 to 0.50% more halogen, based on the total weight of the catalysts, than the second stage.

44. Process in accordance with claim 31, wherein the halogen content of the catalyst varies from one stage to the next, the first stage using a catalyst containing approximately from 0.05 to 0.50% more halogen, based on the total weight of the catalysts, than the second stage.

45. Process in accordance with claim 19, wherein said specific catalyst is used in the last stage.

46. Process in accordance with claim 20, wherein said specific catalyst is used in the last stage.

47. Process in accordance with claim 25, wherein said specific cataysts is used in the last stage.

48. Process in accordance with claim 43, wherein said specific catalyst is used in the last stage.

49. Process in accordance with claim 20, wherein the first stage uses a catalyst containing only platinum as the active metal.

50. Process in accordance with claim 20, wherein the first stage uses a catalyst containing platinum and also silicon as the active metal.

51. Process in accordance with claim 1, wherein the first stage uses a catalyst containing platinum and tin as active metals.

52. Process in accordance with claim 41, wherein the first stage uses a catalyst containing platinum and tin as active metals.

53. Process in accordance with claim 31, wherein the first stage uses a catalyst containing platinum and tin as active metals and also silicon.

54. Process in accordance with claim 20, said specific catalyst further contains from 0.1 to 2% of silicon.

55. Process in accordance with claim 40, said specific catalyst further contains from 0.1 to 2% of silicon.

56. Process in accordance with claim 48, said specific catalyst further contains from 0.1 to 2% of silicon.

57. Application of said process in accordance with claim 20 to the isomerization of alkylaromatic hydrocarbons having eight carbon atoms.

58. Application of said process in accordance with claim 43 to the isomerization of alkylaromatic hydrocarbons having eight carbon atoms.

59. Application of said process in accordance with claim 56 to the isomerization of alkylaromatic hydrocarbons having eight carbon atoms.

60. Application of said process in accordance with claim 20, to the treatment of a charge of alkylaromatic hydrocarbons containing approximately from 5 to 50% by weight of ethylbenzene.

61. Application of said process in accordance with claim 52 to the treatment of a charge of alkylaromatic hydrocarbons containing approximately from 5 to 50% by weight of ethylebenzene.

62. Application of said process in accordance with claim 56 to the treatment of a charge of alkylaromatic hydrocarbons containing approximately from 5 to 50% by weight of ethylbenzene.

* * * * *

UNITED STATES PATENT AND TRADEMARK OFFICE
CERTIFICATE OF CORRECTION

PATENT NO. : 4,152,246
DATED : May 1, 1979
INVENTOR(S) : Weisang et al.

It is certified that error appears in the above-identified patent and that said Letters Patent are hereby corrected as shown below:

Claim 11, column 19, line 37 omit "(a)";

Claim 12, column 19, line 41 "befre" should be --before--;

Claim 19, column 20, line 11 "element1" should be --elemental--;

Claim 27, column 20, line 63 "250" should be --350--;

Claim 41, column 21, line 61 after "0.05%" should be inserted -- to 0.50%--;

Claim 47, column 22, line 18 "catalysts" should be --catalyst--;

Claim 51, column 22, line 27 "1" should be --31--.

Signed and Sealed this

Eighteenth Day of September 1979

[SEAL]

Attest:

LUTRELLE F. PARKER

Attesting Officer Acting Commissioner of Patents and Trademarks